United States Patent [19]
Andersson et al.

[11] Patent Number: 5,981,469
[45] Date of Patent: Nov. 9, 1999

[54] 78 RESIDUE POLYPEPTIDE (NK-LYSINE) AND ITS USE

[76] Inventors: Mats Andersson, Folkungagatan 132, S-116 30 Stockholm; Hans G Boman, Odengatan 23, S-114 24 Stockholm; Hans Jörnvall, Vallstigen 18, S-172 46 Sundbyberg; Viktor Mutt, Jungfrudansen 18, S-171 56 Solna, all of Sweden

[21] Appl. No.: 08/732,228

[22] PCT Filed: Apr. 28, 1995

[86] PCT No.: PCT/SE95/00475

§ 371 Date: Dec. 4, 1996

§ 102(e) Date: Dec. 4, 1996

[87] PCT Pub. No.: WO95/29937

PCT Pub. Date: Nov. 9, 1995

[30] Foreign Application Priority Data

Apr. 29, 1994 [SE] Sweden ................................. 9401480

[51] Int. Cl.$^6$ ........................ C07K 14/00; C07K 14/435
[52] U.S. Cl. ................................ 514/2; 530/200; 530/350
[58] Field of Search .................................. 530/350, 300, 530/323, 324; 514/2, 11

[56] References Cited

PUBLICATIONS

Lehrer et al. (1993) Annu. Rev. Immunol. 11 :105–128.

*Primary Examiner*—Lila Feisee
*Assistant Examiner*—Michael Pak
*Attorney, Agent, or Firm*—Burns, Doane, Swecker & Mathis, L.L.P.

[57] ABSTRACT

A 78 residue polypeptide comprising the following amino acid sequence

GYFCESCRKIIQKLEDMVGPQP-
NEDTVTQAASQVCDKLKILRGLCK-
KIMRSFLRRISWDILTGKK PQAICVDIKICK [SEQ ID NO:1]:

and functional derivatives and pharmaceutically acceptable salts thereof, said sequence comprising intra-linked half-cysteines; pharmaceutical composition containing such polypeptide as an active ingredient; a method for inhibiting microbial growth and cancer cell growth in animals including man; and nucleotide sequence corresponding to such polypeptide.

15 Claims, 5 Drawing Sheets

```
                                                    1                                        40
NKG5                           MATWALLLLAAMLLLGNPGLVFSRLSPEYYDLARAHLRDEEKSCPCLAQEGPQGDLLTKTQEL
                                                                       60                              145
NKG5         GRDYRTCLTIVQKLKKMVD.KPTQRSVSNAATRVCRTGRSRWRDVCRNFMRRYQSRVTQGLVAGETAQQICEDLRLCIPSTGPL
             — :| :|||  |      — :|::|| :  .|: :|| |   :  |: :: | :  |: :|—||—|—|
                                         80                          120
NK-lysin     GYFCESCRKIIQKLEDMVGPQPNEDTVTQAASQVCDKLKI.LRGLCKKIMRSFLRRISWDILTGKKPQAICVDIKICKE
```

NKG5 gene sequenced by Houchins et al., (1993) Immunogenetics 37:102–107.

Fig. 3

```
         10        20        30        40        50        60        70
          |         |         |         |         |         |         |
GAATTCGGCACGAGCTGAGAGCAAGTCTTCTCACTGACAGGGGTTCATTGCAGCCCCAGGGCAGAGTAGGGCTGGGG

I  R  H  E  L  R  A  S  L  L  T  D  R  G  S  L  Q  P  Q  G  R  V  G  L  G
     80        90       100       110       120       130       140       150
      |         |         |         |         |         |         |         |
CCTCCCGGATTCCTCACGAGGGCGCATCCCTGCCCCGCTCCATCTGCTCCATCTGCTCCATCCGGGCGCCTCTGCTG

S  R  I  P  H  E  G  A  S  L  P  R  S  I  C  S  I  C  S  I  R  A  P  L  L
    160       170       180       190       200       210       220       230
      |         |         |         |         |         |         |         |
CTGAGAGAACTGACTTTTCCTCCCCCTCTGCCCTCGGGGATGGGAGTCCTAATGCTCTTTCTTTCCCAGGGCTGGCC

E  R  T  D  F  S  S  P  S  A  L  G  D  G  S  A  N  A  L  S  F  P  G  L  A
    240       250       260       270       280       290       300        31
      |         |         |         |         |         |         |         |
TTTCCGGTCTGACCCCTGAGCACTCTGCCCTGGCAAGGGCCCACCCATGCGACGGAGAGCAGTTCTGCCAGAACCTG

S  G  L  T  P  E  H  S  A  L  A  R  A  H  P  C  D  G  E  Q  F  C  Q  N  L
    320       330       340       350       360       370       380
      |         |         |         |         |         |         |
CCCCGGAGGACCCCCAGGGTGACCAGCTGCTCCAAAGAGAGGAGCTGGGCCTCATCTCTGAGTCTTGTCGGAAGATA

P  E  D  P  Q  G  D  Q  L  L  Q  R  E  E  L  G  L  I  C  E  S  C  R  K  I
       400       410       420       430       440       450       460
         |         |         |         |         |         |         |
TCCAGAAGCTGGAGGACATGGTGGGACCACAACCCAACGAGGACACTGTCACCCAGGCAGCCTCCCGGGTGTGTGAC

Q  K  L  E  D  M  V  G  P  Q  P  N  E  D  T  V  T  Q  A  A  S  R  V  C  D
    470       480       490       500       510       520       530       540
      |         |         |         |         |         |         |         |
AGATGAAGATACTGAGAGGTGTGTGCAAGAAGATCATGAGGACCTTTCTCCGTCGCATCTCCAAGGACATCCTGACT

M  K  I  L  R  G  V  C  K  K  I  M  R  T  F  L  R  R  I  S  K  D  I  L  T
    550       560       570       580       590       600       610       620
      |         |         |         |         |         |         |         |
GGAAGAAACCCCAGGCTATCTGTGTGGACATCAAGATCTGTAAAGAGAAGACAGGTCTCATCTGAGCCCCCGCGTCC

K  K  P  Q  A  I  C  V  D  I  K  I  C  K  E  K  T  G  L  I  -
    630       640       650       660       670       680       690        70
      |         |         |         |         |         |         |         |
CTGACCCCACCATGGAGAAGAAGCACAGAAACTCCAGCACCCTCGGCCGGTTCCTTGCCTCCTAAATCCAGGGTCTG 710       720       730       740       750       760       770
         |         |         |         |         |         |         |
CCTCTTGTTTCTCTCACCTAACTCCTGCCACCGCCCTCCCCTCTCAGGAGAATTAAATGTCATGCAAGATTAAAAAA
                                                               TTTTTTCGAAGAGCTCCTTAAGCT
                                                                 CGAAGAGCTCCTTAAGCT
```

78 RESIDUE POLYPEPTIDE (NK-LYSINE) AND ITS USE

The present invention relates to a new polypeptide, its therapeutic use, pharmaceutical compositions containing same as an active ingredient and a method for inhibiting microbial growth.

The upper part of the small intestine is under normal healthy conditions almost sterile and could therefore be expected to produce antimicrobial peptides. In 1987 a program was started for the identification of such peptides using the large scale fractionation scheme devised for the isolation of peptide hormones produced in the porcine small intestine [Mutt, V. 1986. Question answered and raised by work on the chemistry of gastrointestinal and cerebrogastrointestinal hormonal polypeptides. Chem Scr. 26B: 191–207]. This project has earlier yielded five antibacterial peptides, the present paper describes the sixth one. The two first peptides, cecropin P1 [Lee, J.-Y., A. Boman, S. Chuanxin, M. Andersson, H. Jörnvall, V. Mutt and H. G. Boman. 1989. Antibacterial peptides from pig intestine: Isolation of a mammalian cecropin. Proc. Natl. Sci. USA. 86: 9159–9162] and PR-39 [Agerberth, B., J.-Y. Lee, T. Bergman, M. Carlquist, H. G. Boman, V. Mutt and H. Jörnvall, 1991. Amino Acid Sequence of PR-39—Isolation from Pig Intestine of a New Member of the Family of Proline-Arginine-Rich Antibacterial Peptides. Eur J Biochem. 202: 849–854], showed both potent activity against several Gram-negative bacteria. They also act on *Bacillus megaterium* but they do not act on other Gram-positive bacteria like Staphylococcus. Cecropin P1 was clearly related to the insect cecropins and was related to two proline-rich peptides from bovine phagocytes. The next three peptides to be identified [Agerberth, B., A. Boman, M. Andersson, H. Jörnvall, V. Mutt and H. G. Boman. 1993. Isolation of three antibacterial peptides from pig intestine: gastric inhibitory polypeptide (7–42), diazepam-binding inhibitor (32–86) and a novel factor, peptide 3910. Eur. J. Biochem. 216: 623–629] were active against *B.megaterium* but not against *E.coli* and two of these turned out to be derived from earlier known hormones, GIP (gastric inhibitory polypeptide) and DB1 (diazepam-binding inhibitor).

The intestine is an organ rich in blood vessels and peptides isolated from intestine can originate from blood cells. Thus, PR-39 was recently shown to be produced in the pig bone marrow rather than in the intestine [Storici, P. and M. Zanetti 1993. A cDNA derived from pig bone marrow cells predicts a sequence identical to the intestinal antibacterial peptide PR-39. Biochem. Biophys. Res. Comm. 196: 1058–1065] and this applies also to the protegrin PG-2 [Storici, P. and M. Zanetti, 1993. A cDNA derived from pig bone marrow cells predicts a sequence identical to the intestinal antibacterial peptide PR-39. Biochem. Biophys. Res. Comm. 196: 1058–1065] a peptide earlier isolated from pig phagocytes. Defensin-like peptides, cryptins, have been isolated from murine small intestine and human Paneth cells express a gene for a definsin-like peptide.

Defensins were earlier found in circulating phagocytes of a number of mammals [Lehrer, R. I. and Ganz, T. 1992. Defensins—Endogenous Antibiotic Peptides from Human Leukocytes. In Secondary Metabolites: Their Function and Evolution, p 276–293, Ciba Foundation Symposia No. 171. John Wiley & Sons Ltd., Chichester, PO19 1UD, UK]. Bovine phagocytes contain a number of different peptide antibiotics: A small dodeca peptide with two cysteines called bactenecin [Romeo, D., B. Skerlavaj, M. Bolognesi and R. Gennaro, 1988. Structure and bactericidal activity of an antibiotic dodecapeptide purified from bovine neutrophils. J.Biol.Chem. 263: 9573–9575], two larger Proline-rich peptides, Bac5 and Bac7, [Frank, R. W., R. Gennaro, K. Schneider, M. Przybylski and D. Romeo. 1990. Amino acid sequences of two proline-rich bactenecins Antimicrobial peptides of bovine neutrophils. J.Biol.Chem. 265: 18871–18874] and a tryptophan-rich peptide, indolicidin [Selsted, M. E., M. J. Novotny, W. L. Morris, Y. Q. Tang, W. Smith and J. S. Cullor, 1992. Indolicidin, a Novel Bactericidal Tridecapeptide Amide from Neutrophils. J.Biol.Chem 267: 4292–4295]. Bovine phagocytes also contain 13 different β-defensins [Selsted, M. E., Y.-Q. Tang, W. L. Morris, P. A. McGuire, M. J. Novotny, W. Smith, A. H. Henschen and J. S. Cullor, 1993. Purification, primary structures, and antibacterial activities of β-defensins, a new family of antimicrobial peptides from bovine neutrophils. J.Biol.Chem. 268: 6641–6648], a type first found in bovine trachea [Diamond, G., M. Zasloff, H. Eck, M. Brasseur, W. L. Maloy and C. L. Bevins, 1991. Tracheal anti-microbial peptide, a cysteine-rich peptide from mammalian tracheal mucosa: Peptide isolation and cloning of a cDNA. Proc. Natl. Acad. Sci. USA. 88: 3952–3956]. Peptide antibiotics are common in both invertebrates and vertebrates and they are believed to be important components of the innate immunity in many animals.

In some cases the effect of antibacterial peptides are not restricted to microbes. Defensins are cytolytic to a variety of mammalian cells including tumor cells [Lehrer, R. I., A. K. Lichtenstein and T. Ganz, 1993. Defensins: Antimicrobial and cytotoxic peptides of mammalian cells. Annu Rev Immunol. 11: 105–128] and bactenecin (contrary to peptides like cecropin P1, magainin and apidaecin) was recently shown to exhibit a selective toxicity for neuronal and glia cells [Radermacher, S. W., V. M. Schoop and H. J. Schluesener. 1993. Bactenecin, a leukocytic antimicrobial peptide, is cytotoxic to neuronal and glial cells. Journal of Neuroscience Research. 36: 657–662].

The present invention has for its object to provide a new polypeptide which is biologically active.

Another object of the invention is to provide a new polypeptide having antimicrobial activity against bacteria and also lytic activity vis-à-vis several human cancer cell lines.

Yet another object of the invention is to provide pharmaceutical compositions containing such polypeptide as an active ingredient.

A further object of the invention is to provide a nucleotide sequence which in an appropriate expression system is capable of expressing such polypeptide.

Still another object of the invention is to provide a method for inhibiting microbial growth and growth of cancer cells in animals including man.

For these and other objects that will be clear from the following disclosure the invention provides for a polypeptide comprising the following amino acid sequence:

GYFCESCRKIIQKLEDMVGPQP-
    NEDTVTQAASQVCDKLKILRGLCKKIMRSFLRRISW
    DILTGKKPQAICVDIKICKE     [SEQ ID NO:1]

including also functional derivatives thereof. In said sequence the half-cystines are intra-linked as; shown in FIG. 3.

Figure 4:
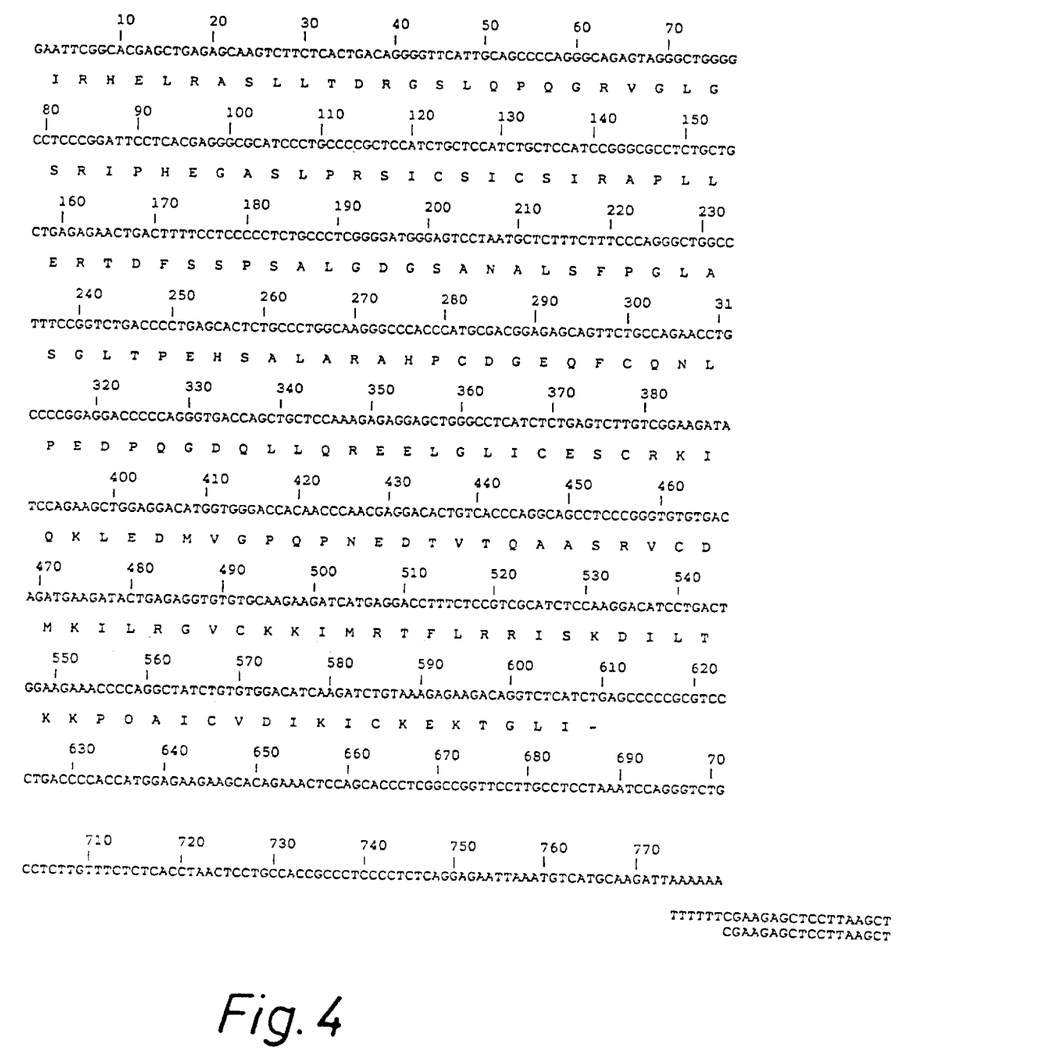
FIG. 4 [SEQ ID NOS:5–7] illustrates the nucleotide sequence corresponding to NK-lysine.
Figure 5:
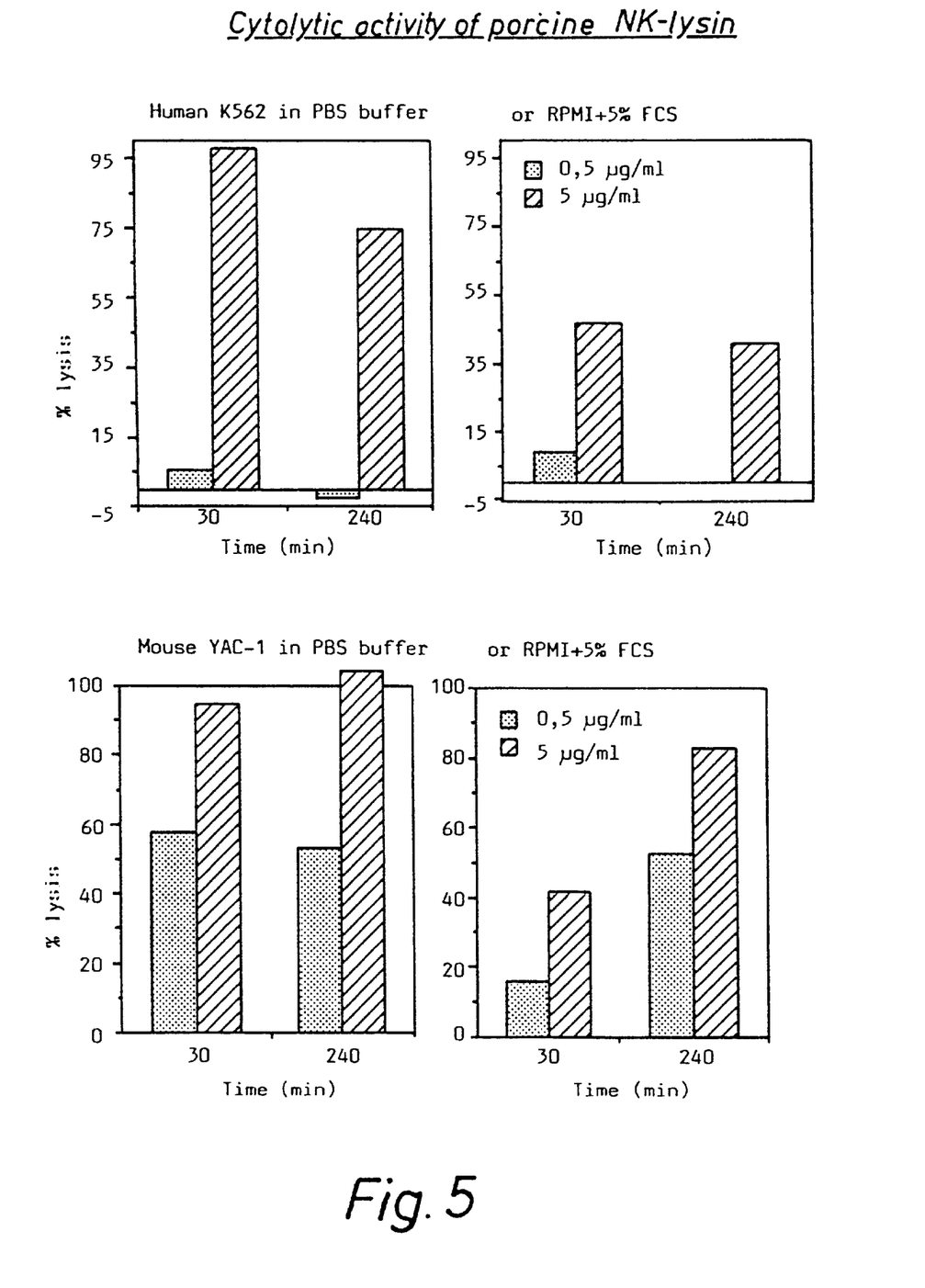
FIG. 5 illustrates a diagram showing the cytolytic activity of NK-lysine against two tumor cell lines.

The new polypeptide according to the invention finds therapeutic applications, such as use as an antimicrobial agent or use based on its lytic activity against NK sensitive tumor cell lines of murine or human origin (see FIG. 4). The lytic activity is particularly useful against tumor cell lines of murine or human origin.

The invention also covers a pharmaceutical composition containing as an active ingredient the polypeptide as defined above in an effective amount together with a pharmaceutically acceptable carrier or diluent.

Said amount is suitably antimicrobially active, such as antibacterially active. The carrier or diluent is preferably adapted for oral, intraveneous, intramuscular or subcutaneous administration.

Finally, the invention includes a method for inhibiting microbial growth in animals, such as mammals including man, said method comprising the step of administering to an animal subject to a disorder caused by microbial attack a polypeptide as defined above, a functional derivative thereof or a composition as defined above in an inhibitory amount.

Such method can be directed to inhibiting tumor cell growth in animals or can be directed to intestinal use constituted by oral administration of a composition as defined above in a slow release form. The method can also be directed to administration by injection of such a composition in an injectible dose form.

With regard to the expression "functional derivatives thereof" it is well known in regard to the technical area to which the present invention pertains that minor amino acid substitutions can be made to the polypeptide which do not affect or do not substantially affect the function of the polypeptide. Determination of conceivable substitutions is accomplished according to procedures well known to those skilled in the art. Thus, all polylpeptides having substantially the same amino acid sequence and substantially the same biological activity, such as antimicrobial and lytic activity, are within the scope of this invention.

Also within the scope of the present invention are pharmaceutically acceptable salts of the polypeptides of this invention. Such salts are formed by methods well known to skilled artisans. Thus, for example base salts of the polypeptides can be prepared according to conventional methods. When in the instant disclosure including the claims the term polypeptide is used said term is intended to include both functional derivatives and pharmaceutically acceptable salts of the polypeptide.

The active polypeptide according to the present invention can be formulated for use in human or veterinary medicine for therapeutic or prophylactic use. The active preparations are normally administered orally, rectally or parenterally, such as by injection in the form of a pharmaceutical preparation or composition comprising the active constituents in combination with a pharmaceutically acceptable carrier which may be solid, semi-solid or liquid, or contained in a capsule, such as when orally administered. The administration may also take the form of topical application. As examples of pharmaceutical preparations there may be mentioned tablets, drops, solutions and suppositories. Usually, the active constituent constitutes the minor part of the preparation, such as from about 0.1 to about 50% thereof based on weight.

In order to prepare pharmaceutical compositions in the form of dose units for oral application the polypeptide of the invention can be mixed with a solid, pulverulent or other carrier, for example lactose, saccharose, sorbitol, mannitol, starch, such as potatoe starch, corn starch, millopectine, cellulose derivative or gelatine, and may also include lubricants, such as magnesium or calcium stearate, or polyethylene glycol waxes compressed to the formation of tablets or bodies for dragées. The dose units may also be presented in a coated form of enteric type.

By using several layers of the carrier or diluent tablets operating with slow release can be prepared.

Liquid preparations for oral application or for injection can be made in the form of elexirs, syrups or suspensions, for example solutions containing from 0.1 to 20% by weight of active substance, sugar and a mixture of ethanol, water, glycerol, propyleneglycol and possibly other additives of a conventional nature.

The dose by which the active constituent is administered may vary within wide limits and is dependent on different factors, such as the seriousness of the disorder, the age and the weight of the patient and can be adjusted individually.

The invention will now be described by non-limiting examples with reference to the appended drawings, wherein.

MATERIALS AND METHODS USED EXPERIMENTALLY

Materials

Carboxymethyl-cellulose CM 23 (CM-cellulose) was from Whatman (Kent, UK) and Sephadex G-25 from Pharmacia (Uppsala, Sweden). Trypsin (EC 3.4.21.4) seq. grade, endoproteinase Lys-C (ERC 3.4.21.50), endoproteinase Asp-N (EC 3.4.24.-) seq. grade and endoproteinase Glu-C (EC 3.4.21.19) from Boehringer Mannheim (Mannheim, FRG).

Antibacterial Assays

Activity was recorded by the inhibition zone assay in thin agarose plates seeded with *Escherichia coli* strain D21 [Hultmark, D., Å. Engström, K. Andersson, H. Steiner, H. Bennich and H. G. Boman. 1983. EMBO J. 2: 5171–576]. A standard curve was made from known amounts of synthetic cecropin A and 1000 units was defined as an activity equal to that of 1 $\mu$g of cecropin A. The chromatographic fractions were lyophilized and a sample of each fraction was redissolved in 10 $\mu$l water and 3 $\mu$l was used for each assay. For comparison of activities against different bacteria, lethal concentrations (LC values) were calculated from a series of dilutions. LC-values were determined from inhibition zones in plates with LB medium supplemented with Med E (with final concentrations of 0.81 mM $MgSO_4$, 9.5 mM citric acid, 57 mM $K_2HPO_4$ and 16.7 mM $NaNH_4HPO_4$) which increased the activity against *E.coli*. Strain Bd2221/75 of *E.coli* is pathogenic for piglets and originates from the collection of Olof Söderlund, SVA, Uppsala, Sweden.

Purification

The starting material was a concentrate of thermostable intestinal peptides, CTIP, prepared from the upper part of the porcine small intestine [Chen, Z.-w., B. Agerberth, K. Gell, M. Andersson, V. Mutt, C.-G. Östenson, S. Efendic, J. Barros-Söderling, B. Persson and H. Jörnvall. 1988. Isolation and characterization of porcine diazepam-binding inhibitor, a polypeptide not only of cerebral occurrence but also common in intestinal tissues, and with effects on regulation of insulin release. [Eur.J.Biochem. 174: 239–245; Mutt, V. 1959. Preparation of highly purified secretin. Ark.Kemi. 15: 69–74]. An aqueous solution of CTIP was fractionated with ethanol as described [Lee, J.-Y., A. Boman, S. Chuanxin, M. Andersson, H. Jörnvall, V. Mutt and H. G. Boman. 1989. Antibacterial peptides from pig intestine: Isolation of a mammalian cecropin. Proc.Natl.Acad. of Sci. USA. 86: 9159–9162]. The precipitate obtained at −20° C. was dissolved in 0.02 M sodium phosphate pH 6.4 and peptides from the solution was adsorbed to CM-cellulose. After washing with 0.2 M NaCl, a peptide fraction was eluted with 0.2 M HCl, the pH of the eluate adjusted to 4 with sodium acetate and peptides precipitated by saturation with NaCl. This precipitate was dissolved in 0.2 M acetic acid and chromatographed on Sephadex G-25 (10×150 cm).

The eluate corresponding to low molecular weight components was lyophilized before further purification by reversed-phase HPLC on preparative Vydac 218TP152022 column (22×250 mm; The separation Group, Hesperia, Calif.) and for final purification an analytical Vydac 218TP54 column (4.6×250 mm). HPLC chromatography was performed on Waters instruments and absorbance was detected at 214 nm or simultaneously at 214 nm and 280 nm.

Structural Analysis

Purity of the peptides isolated was ascertained by capillary zone electrophoresis with Beckman P/ACE 2000 [Bergman, T., B. Agerberth and H. Jörnvall. 1991. Direct analysis of peptides and amino acids from capillary electrophoresis. FEBS lett. 283: 100–103]. Total composition was determined with an LKB 4251 Alpha Plus amino acid analyzer after hydrolysis in evacuated tubes with 6 M HCl/0.5% phenol at 110° C. for 22 h.

Peptides were carboxymetylated with iodoacetamid or iodoacetic acid [Agerberth, B., J. Barros-Söderling, H. Jörnvall, Z.-w. Chen, C.-G. Östenson, S. Efendic and V. Mutt. 1989. Isolation and characterization of a 60-residue intestinal peptide structurally related to the pancreatic secratory type of trypsin inhibitor: Influence on insulin secretion. Proc.Natl.Acad.Sci. USA. 86: 8590–8594] and desalted on Seppak C18 (Waters, Milford, USA). Carboxymetylated peptides were cleaved enzymatically with endoproteinase Asp-N (in 10% acetonitrile/1% $NH_4HCO_3$ for 24 h at 35° C.) and endoproteinase Lys-C (in 1% $NH_4HCO_3$ for 8 h at 37° C.) at an enzyme/peptide ratio of 1:20 (w/w) or chemically with CNBr in 70% formic acid for 20 hr. Enzymatic digestion of 18 nmol of intact NK-lysine for determination of cysteine-cysteine bridges was performed with trypsin (in 0.1% $NH_4HCO_3$ for 6 h at 37° C., enzyme/peptide ratio; 1:15 (w/w)) and after HPLC-purification, one fragment was incubated with endoproteinase Glu-C (in 0.5% $NH_4HCO_3$ for 16 h at 37° C., enzyme/peptide ratio; 1:2 (w/w)). All fragments were separated by HPLC on Vydac 218TP54 (4.6×250 mm). Edman degradation of intact peptide or fragments thereof were carried out with an ABJ 447 A machine. Peptide mass was determined using a plasma-desorption time-of-flight mass spectrometer (Biolon 20) or Electrospray analysis performed by Rannar Sillard, Niedersächsisches Institut für Peptid-Forschung, Hannover, Germany.

Computer Analyses of the Sequences

Sequences searches and analyses were performed using the GCG program package (version 7.2) [Devereaux, J., P. Haebrli and O. Smithies. 1984. Nucleic Acids Res. 12: 387–395].

EXAMPLE 1

Isolation

Figures 1A, 1B, 1C, 1D:
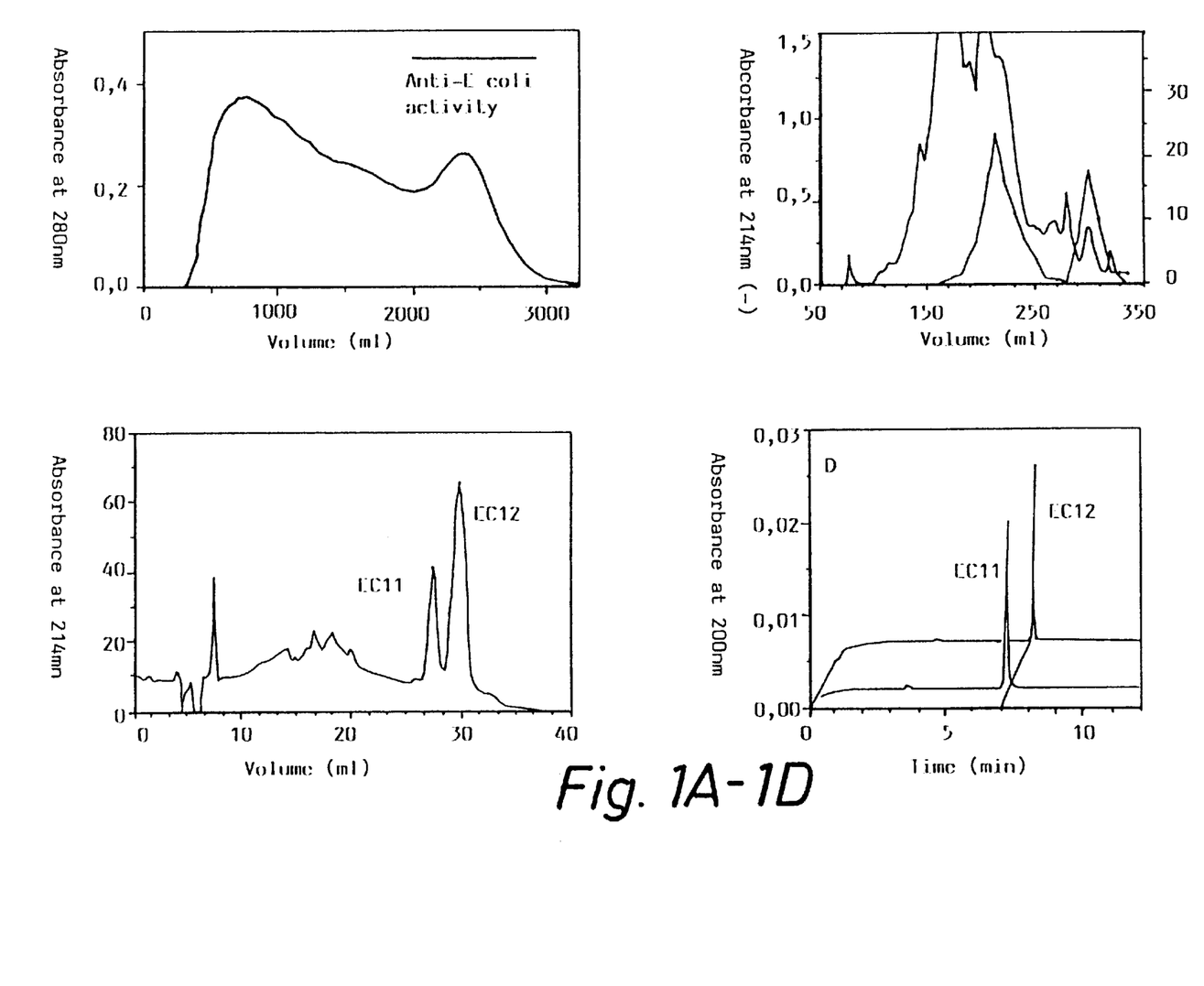
FIGS. 1A to 1D illustrate purification of NK-lysine.

NK-lysine was isolated from an acid extract of boiled pig intestine. A concentrate of thermostable intestinal peptides, CTIP, was prepared and after redissolving in water, a peptide fraction obtained on ethanol fractionation and cation-exchange chromatography. The basic fraction (11.4 g) eluted by 0.2 M HCl was subjected to size exclusion chromatography and the low molecular weight fraction was found to contain antibacterial activity against E.coli and B. Megaterium (FIG. 1A, represented by the bar). In FIG. 1A the basic fraction eluting from CM-cellulose chromatography was dissolved in 0.2 M acetic acid and fractionated by gelfiltration on a Sephadex G-25.

The peptides in this fraction were then further separated by repetitive runs on a preparative RP-HPLC column using in acetronitrile/0.1% trifluoroacetic acid as elutant (FIG. 1B). In FIG. 1B peptides eluting as indicated by the bar in (A) were applied to a semipreparativ Vydac 218TP column. The sample was eluted from the column at a flow of 10 ml/min with a linear gradient of 20–50% B in 30 min and then 50–70% B in 5 min (A=0.1% trifluoroacetic acid, B=acetonitrile).

Two main fractions showed high antimicrobial activity against E.coli. Peptides eluting after 220 ml contained a high degree of arginine and proline and was also found to coelute with a recently isolated peptide, PR-39 [Agerberth, B., J. Y. Lee, T. Bergman, M. Carlquist, H. G. Boman, V. Mutt and H. Jörnvall. 1991. Amino Acid Sequence of PR-39— Isolation from Pig Intestine of a New Member of the Family of Proline-Arginine-Rich Antibacterial Peptides. Eur.J.Biochem. 202: 849–854], when analyzed on capillary electrophoresis. The peptides eluting at a higher concentration of acetonitrile (300 ml) was subjected to a final purification by analytical reverse-phase HPLC, this time with 0.1% heptafluorobutyric acid in acetronitrile as elutant (FIG. 1C). In FIG. 1C the relevant fraction was lyophilized and applied to an analytical Vydac 218TP54 column, eluted at 1 ml/min with a linear gradient of 40–60% D in 5 min and then 60–80% D in 30 min (C=0.1% heptafluorobutyric acid, D=80% acetonitrile/0.1% heptafluorobutyric acid). As can be seen from the figure, two components are separated named NK-lysine (A) and des-Gly-1 NK-lysine (B). The yields were 3.9 mg and 1.2 mg, respectively, after lyophilization. Both peptide eluted as single peaks in capillary zone electrophoresis as shown in FIG. 1D.

Figure 2:
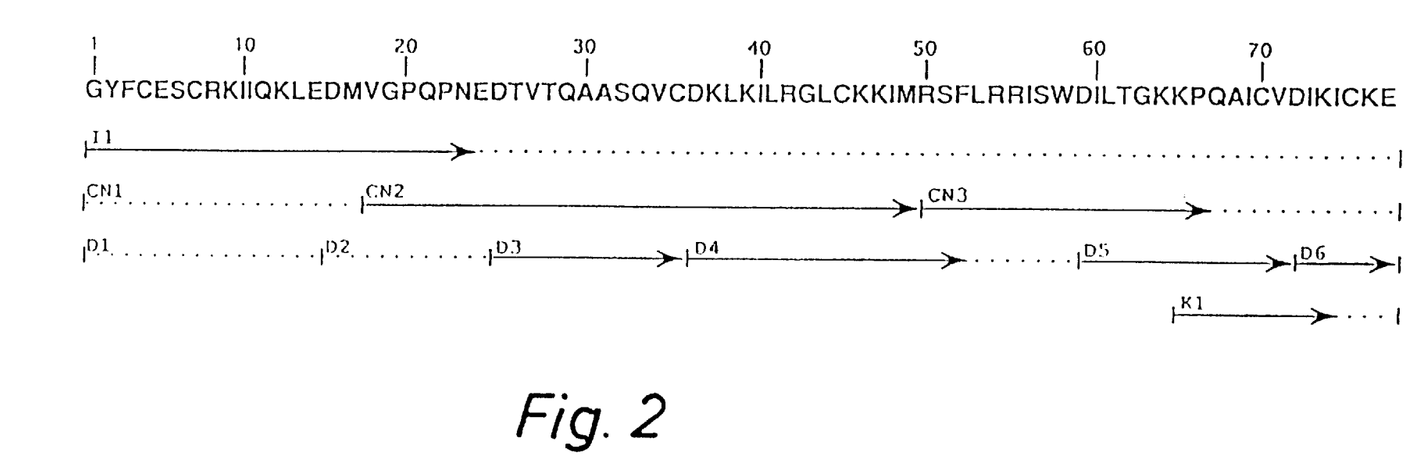
FIG. 2 [SEQ ID NO.:1] illustrates structural analysis of NK-lysine.

By combining the sequence data from intact peptide and overlapping fragments generated enzymatically or chemically, the entire sequence of 78 amino acids for NK-lysine was obtained (FIG. 2 [SEQ ID NO:1]). In this figure the fragmentation was made with cyanobromide (CN1–CN3), Asp-N (D1–D6) and Lys-C (K1). I1 represent intact peptide. Solid lines with arrows show the sequenced regions and dotted lines are fragments in agreement with total amino acid composition. K1 was generated after fragmentation of CN3. Electrospray mass spectrometry measurement yielded a monoisotopic mass of 8923.2±1 which is in good agreement with the molecular mass of 8924.8 calculated from sequence data (assuming that the six cysteines form three intramolecular linkage). Total amino acid analysis was performed on both NK-lysine and des-Gly-1 NK-lysine in their native state and after oxidation by performic acid (Data not shown). Results for NK-lysine were in agreement with sequence data and des-Gly-1 NK-lysine showed a striking similarity to NK-lysine. Mass spectrometry analysis of des-Gly-1 NK-lysine evidenced a monoisotopic mass of 8866.3±1 indicating a difference of 56.9 compared to EC 12, which is identical to the mass of a glycine. Edman degradation of des-Gly-1 NK-lysine identified a peptide identical to des-Gly 1 NK-lysine for the first 18 amino acids.

Figure 3:
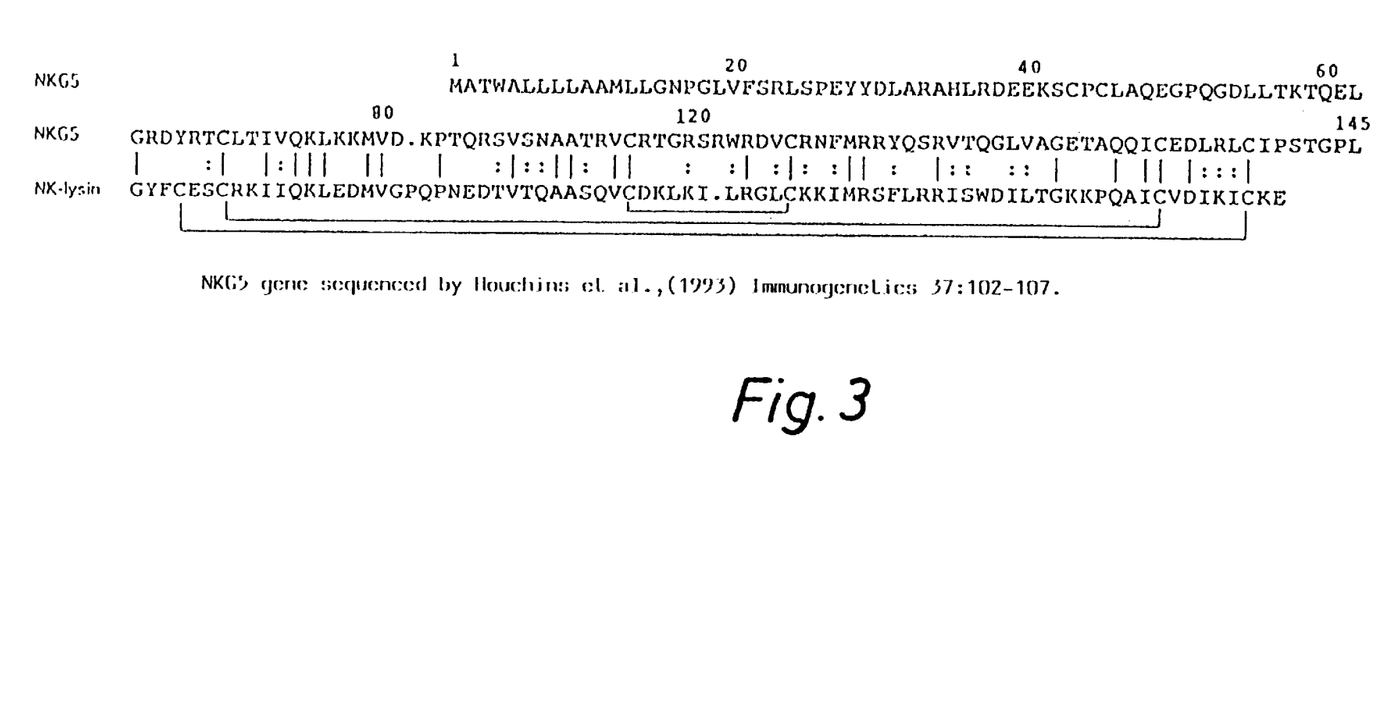
FIG. 3 [SEQ ID NOS:4&1 respectively] shows an alignment analysis of NK-lysine and NKG5.

For determination of disulfide linkage, native NK-lysine was enzymatically digested with trypsin and one tryptic fragment thereafter with endoproteinase Glu-C. The products of both digests were purified by HPLC and peptides containing half-cystein were analysed by sequencer degradation. Results showed that segment S6CRK are associated with K65PQAICVDIK suggesting [SEQ ID NO:2] a bond between Cys7 and Cys70. Likewise G1YFCE [SEQ ID NO.:3] was identified together with 175CKE (cys4–cys76) and L14EDM together with G43LCK (cys35–cys45). These results are consistent with a disulfide bridge pattern of Cys1–Cys6, Cys2–Cys5 and Cys3–Cys4 (FIG. 3 [SEQ ID NOS.4&1, respectively]). In this figure the peptides were aligned with the program PILEUP. Identical amino acids are shown in boxes. Disulfide bridges in NK-lysine are marked by solid lines.

EXAMPLE 2
Antibacterial Activity

We used an inhibition zone assay in agarose gels to test the purified peptides against several strains of bacteria. Both peptides killed Gram-negative and Gram-positive bacteria. The antibacterial spectra as well as the lethal concentrations (the LC-value, the lowest concentration that would be lethal for the bacteria) for both peptides were found to be almost identical (Table 1). High activity was found against *E.coli* and *B. megaterium*. There was no activity against *Pseudomonas aeruginosa* and *Staphylococcus aureus*, but only a limited number of species were tested. The presence of a high salt concentration (with medium E added to the assay plates) increased the activity against *E.coli* (LC-values decreased about 10 times). A pig pathogenic strain of *E.coli* (Bd2221/75) was almost 20 times more resistant to NK-lysine than our normal assay strain D21 (LC-values were 10 $\mu$M compared to 0.54 M).

NK-lysine was also found to have antifungal activity and the LC value for *Candida albicans* was 30 $\mu$M, the same as found for defensin, NP-2. Neither peptide gave a lytic zone on sheep red blood cells at a concentration of 170 $\mu$M.

EXAMPLE 3
Cytotoxicity

Since defensins have cytotoxic effects on mammalian cells, we tested NK-lysine also for cytolytlic activity against two tumor cell lines known to be sensitive to lysis by NK cells, YAC-1 from mouse and K562 from human. The respective cells were labelled with $^{51}$Cr, incubated for different times with NK-lysine (5 $\mu$g/ml), with and without fetal calf serum, then the $^{51}$Cr released was recorded. FIG. 4 shows that YAC-1 was somewhat more sensitive than K562, but both cell lines were quite sensitive to NK-lysine.

EXAMPLE 4
Computer Analysis of the Sequence

Sequence search in swissprotein database (release 27) with the FASTA program revealed that the NK-lysine showed some homology to two polypeptides, NKG5 and 519, deduced from two cDNA sequences isolated from activated human T and NK cells products [Yabe, T., C. McSherry, F. H. Bach and J. P. Houchins. 1990. A cDNA clone expressed in natural killer and T cells that likely encodes a secreted protein. J.Exp.Med. 172: 1159–1163; Jongstra, J., T. J. Schall, B. J. Dyer, C. Clayberger, J.Jorgensen, M. M. Davis and A. M. Krensky. 1987. The isolation and sequence of a novel gene from a human functional T cell line. J.Exp.Med. 165: 601–614]. These postulated proteins have 33% identity and 66% similarity when aligned with the program BESTFIT (FIG. 3). Sequences were aligned to NK-lysine with PILEUP and consensus sequence created by PROFILEMAKE. Similarities to the consensus sequence was searched in EMBL database (release 32) with PROFIELSEARCH.

EXAMPLE 5

Nucleotide Sequence

In FIG. 4 [SEQ ID NOS. 5–7] there is illustrated the nucleotide sequence of clones corresponding to NK-lysine. The open reading frame corresponding to the peptide is indicated by dotted underlining. The two primers used in the second step of the synthesis (bp 402 to 420 and 565 to 582) are fully underlined, whereas the preliminary probe (bp 532 to 550) is underlined in heavy dots.

TABLE 1

Antimicrobial activity of two NK-lysins from pig intestine

| | | Lethal conc. ($\mu$M) for Peptides | | | |
|---|---|---|---|---|---|
| | | NK-lysin | | DesG1-NK-lys. | |
| Bact. and fungal species | Strain | +Med. E | −Med. E | +Med. E | −Med. E |
| *Escherichia coli* | D21 | 0.5 | 8 | 0.8 | 10 |
| *Escherichia coli* | Bd2221/75 | 10 | 39 | 11 | 40 |
| *Pseudomonas aeruginosa* | OT97 | >190 | Nd | >160 | Nd |
| *Acinetobacter calcoaceticus* | Ac11 | 7 | Nd | 12 | Nd |
| *Bacillus megaterium* | Bm11 | 1.6 | 0.8 | 1.4 | 0.9 |
| *Staphylococcus aureus* | Cowan I | Nd | >190 | Nd | >160 |
| *Streptococcus pyogenes* | w.t. | Nd | 34 | Nd | 30 |
| *Candida albicans* | w.t. | Nd | 31 | Nd | Nd |

Lethal concentration is the lowest concentration that will kill the bacteria.

Obtained from inhibition zone of a dilution series (Hultmark, D., A. Engström, K. Andersson, H. Steiner, H. Rennich and H. G. Boman, 1983. EMBO J. 2: 571–576)

We claim:

1. A biologically pure polypeptide having antimicrobial activity comprising the following amino acid sequence GYFCESCRKIIQKLEDMVGPQP-
NEDTVTQAASQVCDKLKILRGLCKKIMRSFL RRISWD-
ILTGKKPQAICVDIKICKE (SEQ ID NO. 1):

2. A biologically pure polypeptide according to claim 1 which is suitable for use as a therapeutic agent.

3. A polypeptide which consists of the amino acid sequence having SEQ ID NO. 1.

4. A pharmaceutical composition containing as an active ingredient the antimicrobial polypeptide according to claim 1 in an antimicrobially effective amount together with a pharmaceutically acceptable carrier or diluent.

5. A pharmaceutical composition according to claim 4, wherein said amount is antibacterially active.

6. A pharmaceutical composition according to claim 5, wherein said carrier or diluent is suitable for oral, intravenous, intramuscular or subcutaneous administration.

7. A pharmaceutical composition according to claim 4, wherein said carrier or diluent is suitable for oral, intravenous, intramuscular or subcutaneous administration.

8. A method for inhibiting microbial growth in a subject in need of such inhibition comprising administering an effective antimicrobial amount of the polypeptide according to claim 1.

9. A method according to claim 8 for inhibiting bacterial growth.

10. A method according to claim 9 for intestinal use comprising oral administration of a pharmaceutical composition containing said polypeptide as an active ingredient in an effective antibacterial amount together with a pharmaceutically acceptable carrier or diluent in a slow release form.

11. A method according to claim 8 for intestinal use comprising oral administration of a pharmaceutical composition containing said polypeptide as an active ingredient in an antimicrobial effective amount together with a pharmaceutically acceptable carrier or diluent in a slow release form.

12. A method according to claim 8, comprising administration by injection of a composition containing said polypeptide as an active ingredient in an effective antimicrobial amount together with a pharmaceutically acceptable carrier or diluent in an injectable dose form.

13. A method according to claim 8, comprising administration by injection of a composition containing said polypeptide as an active ingredient in an effective antimicrobial amount together with a pharmaceutically acceptable carrier or diluent in an injectable dose form.

14. The method according to claim 8, wherein said polypeptide consists of the amino acid sequence having SEQ ID NO. 1.

15. A method for inhibiting microbial growth in a subject in need of such inhibition comprising administering an effective antimicrobial amount of the polypeptide according to claim 4.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 78 amino acids
       (B) TYPE: amino acid
       (C) STRANDEDNESS: single
       (D) TOPOLOGY: linear     (ii) MOLECULE TYPE: peptide     (xi) SEQUENCE DESCRIPTION: SEQ ID NO:1:

```
Gly Tyr Phe Cys Glu Ser Cys Arg Lys Ile Ile Gln Lys Leu Glu Asp
1               5                   10                  15

Met Val Gly Pro Gln Pro Asn Glu Asp Thr Val Thr Gln Ala Ala Ser
                20                  25                  30

Gln Val Cys Asp Lys Leu Lys Ile Leu Arg Gly Leu Cys Lys Lys Ile
                35                  40                  45

Met Arg Ser Phe Leu Arg Arg Ile Ser Trp Asp Ile Leu Thr Gly Lys
                50                  55                  60

Lys Pro Gln Ala Ile Cys Val Asp Ile Lys Ile Cys Lys Glu
65                  70                  75
```

(2) INFORMATION FOR SEQ ID NO:2:

(i) SEQUENCE CHARACTERISTICS:
       (A) LENGTH: 9 amino acids
       (B) TYPE: amino acid
       (C) STRANDEDNESS: single
       (D) TOPOLOGY: linear     (ii) MOLECULE TYPE: peptide     (xi) SEQUENCE DESCRIPTION: SEQ ID NO:2:

```
Pro Gln Ala Ile Cys Val Asp Ile Lys
1               5
```

(2) INFORMATION FOR SEQ ID NO:3:

(i) SEQUENCE CHARACTERISTICS:
       (A) LENGTH: 4 amino acids
       (B) TYPE: amino acid
       (C) STRANDEDNESS: single
       (D) TOPOLOGY: linear     (ii) MOLECULE TYPE: peptide     (xi) SEQUENCE DESCRIPTION: SEQ ID NO:3:

```
Tyr Phe Cys Glu
1
```

(2) INFORMATION FOR SEQ ID NO:4:

(i) SEQUENCE CHARACTERISTICS:
       (A) LENGTH: 145 amino acids
       (B) TYPE: amino acid
       (C) STRANDEDNESS: single
       (D) TOPOLOGY: linear     (ii) MOLECULE TYPE: peptide     (xi) SEQUENCE DESCRIPTION: SEQ ID NO:4:

```
Met Ala Thr Trp Ala Leu Leu Leu Ala Ala Met Leu Leu Gly Asn
1               5                   10                  15

Pro Gly Leu Val Phe Ser Arg Leu Ser Pro Glu Tyr Tyr Asp Leu Ala
            20              25              30

Arg Ala His Leu Arg Asp Glu Lys Ser Cys Pro Leu Ala Gln
        35              40              45

Glu Gly Pro Gln Gly Asp Leu Leu Thr Lys Thr Gln Glu Leu Gly Arg
 50              55                  60

Asp Tyr Arg Thr Cys Leu Thr Ile Val Gln Lys Leu Lys Lys Met Val
65              70                  75                  80

Asp Lys Pro Thr Gln Arg Ser Val Ser Asn Ala Ala Thr Arg Val Cys
                85              90              95

Arg Thr Gly Arg Ser Arg Trp Arg Asp Val Cys Arg Asn Phe Met Arg
            100             105             110

Arg Tyr Gln Ser Arg Val Thr Gln Gly Leu Val Ala Gly Glu Thr Ala
            115             120             125

Gln Gln Ile Cys Glu Asp Leu Arg Leu Cys Ile Pro Ser Thr Gly Pro
130             135                 140

Leu
145

(2) INFORMATION FOR SEQ ID NO:5:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..78

(ix) FEATURE:
        (A) NAME/KEY: CDS
        (B) LOCATION: 80..154

(ix) FEATURE:
        (A) NAME/KEY: CDS
        (B) LOCATION: 157..231

(ix) FEATURE:
        (A) NAME/KEY: CDS
        (B) LOCATION: 234..308

(ix) FEATURE:
        (A) NAME/KEY: CDS
        (B) LOCATION: 311..385

(ix) FEATURE:
        (A) NAME/KEY: CDS
        (B) LOCATION: 388..462

(ix) FEATURE:
        (A) NAME/KEY: CDS
        (B) LOCATION: 465..539

(ix) FEATURE:
        (A) NAME/KEY: CDS
        (B) LOCATION: 542..604

(xi) SEQUENCE DESCRIPTION: SEQ ID NO:5:

GA ATT CGG CAC GAG CTG AGA GCA AGT CTT CTC ACT GAC AGG GGT TCA         47
   Ile Arg His Glu Leu Arg Ala Ser Leu Leu Thr Asp Arg Gly Ser
   1               5                   10                  15
```

```
TTG CAG CCC CAG GGC AGA GTA GGG CTG GGG  C C TCC CGG ATT CCT CAC    94
Leu Gln Pro Gln Gly Arg Val Gly Leu Gly     Ser Arg Ile Pro His
             20                  25                           30

GAG GGC GCA TCC CTG CCC CGC TCC ATC TGC TCC ATC TGC TCC ATC CGG   142
Glu Gly Ala Ser Leu Pro Arg Ser Ile Cys Ser Ile Cys Ser Ile Arg
             35                  40                  45

GCG CCT CTG CTG CT GAG AGA ACT GAC TTT TCC TCC CCC TCT GCC CTC    189
Ala Pro Leu Leu    Glu Arg Thr Asp Phe Ser Ser Pro Ser Ala Leu
             50                  55                  60

GGG GAT GGG AGT CCT AAT GCT CTT TCT TTC CCA GGG CTG GCC           231
Gly Asp Gly Ser Pro Asn Ala Leu Ser Phe Pro Gly Leu Ala
             65              70              75

TT TCC GGT CTG ACC CCT GAG CAC TCT GCC CTG GCA AGG GCC CAC CCA    278
   Ser Gly Leu Thr Pro Glu His Ser Ala Leu Ala Arg Ala His Pro
            80                  85                  90

TGC GAC GGA GAG CAG TTC TGC CAG AAC CTG CC  CCG GAG GAC CCC CAG   325
Cys Asp Gly Glu Gln Phe Cys Gln Asn Leu     Pro Glu Asp Pro Gln
             95                  100                    105

GGT GAC CAG CTG CTC CAA AGA GAG GAG CTG GGC CTC ATC TCT GAG TCT   373
Gly Asp Gln Leu Leu Gln Arg Glu Glu Leu Gly Leu Ile Ser Glu Ser
             110                 115                 120

TGT CGG AAG ATA TC CAG AAG CTG GAG GAC ATG GTG GGA CCA CAA CCC    420
Cys Arg Lys Ile    Gln Lys Leu Glu Asp Met Val Gly Pro Gln Pro
             125                 130                 135

AAC GAG GAC ACT GTC ACC CAG GCA GCC TCC CGG GTG TGT GAC           462
Asn Glu Asp Thr Val Thr Gln Ala Ala Ser Arg Val Cys Asp
             140             145             150

AG ATG AAG ATA CTG AGA GGT GTG TGC AAG AAG ATC ATG AGG ACC TTT    509
   Met Lys Ile Leu Arg Gly Val Cys Lys Lys Ile Met Arg Thr Phe
            155                 160                 165

CTC CGT CGC ATC TCC AAG GAC ATC CTG ACT GG AAG AAA CCC CAG GCT    556
Leu Arg Arg Ile Ser Lys Asp Ile Leu Thr    Lys Lys Pro Gln Ala
             170                 175                 180

ATC TGT GTG GAC ATC AAG ATC TGT AAA GAG AAG ACA GGT CTC ATC TGA   604
Ile Cys Val Asp Ile Lys Ile Cys Lys Glu Lys Thr Gly Leu Ile *
             185                 190                 195

GCCCCCCGCG TCCCTGACCC CACCATGGAG AAGAAGCACA GAAACTCCAG CACCCTCGGC  664

CGGTTCCTTG CCTCCTAAAT CCAGGGTCTG CCTCTTGTTT CTCTCACCTA ACTCCTGCCA  724

CCGCCCTCCC CTCTCAGGAG AATTAAATGT CATGCAAGAT TAAAAAA               771

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TTTTTTCGAA GAGCTCCTTA AGCT                                         24

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

-continued (ii) MOLECULE TYPE: DNA (genomic)

(xi) SEQUENCE DESCRIPTION: SEQ ID NO:7:

CGAAGAGCTC CTTAAGCT 18